United States Patent [19]

Webster

[11] Patent Number: 4,585,344

[45] Date of Patent: Apr. 29, 1986

[54] DISCHARGE CELL FOR OPTOGALVANIC SPECTROSCOPY HAVING ORTHOGONAL RELATIONSHIP BETWEEN THE PROBE LASER AND DISCHARGE AXIS

[75] Inventor: Christopher R. Webster, Pasadena, Calif.

[73] Assignee: The United States of America as represented by the Administrator of the National Aeronautics and Space Administration, Washington, D.C.

[21] Appl. No.: 556,514

[22] Filed: Nov. 30, 1983

[51] Int. Cl.$^4$ .................. G01J 3/443; G01N 21/66
[52] U.S. Cl. .................................. 356/311; 356/318
[58] Field of Search ............... 356/300, 311, 313, 314, 356/316–318

[56] References Cited

U.S. PATENT DOCUMENTS

| 4,148,586 | 4/1979 | Green et al. | 250/423 P X |
| 4,166,219 | 8/1979 | Ausschitt | 250/423 P |
| 4,402,606 | 9/1983 | Zalewski | 356/318 |
| 4,548,496 | 10/1985 | Roberts et al. | 356/213 |

OTHER PUBLICATIONS

Cartwright, *Journal of Physics E*, vol. 9, No. 2, Feb. 1976, pp. 92 and 93.

Primary Examiner—F. L. Evans
Attorney, Agent, or Firm—Paul F. McCaul; Thomas H. Jones; John R. Manning

[57] ABSTRACT

Disclosed is a method and apparatus for an optogalvanic spectroscopy system. Orthogonal geometry exists between the axis of a laser probe beam and the axis of a discharge created by a pair of spaced-apart and longitudinally aligned high voltage electrodes. The electrodes are movable to permit adjustment of the location of a point in the discharge which is to be irradiated by a laser beam crossing the discharge region. The cell dimensions are selected so that the cross-section of the discharge region is substantially comparable in size to the cross-section of the laser beam passing orthogonally through the discharge region.

8 Claims, 9 Drawing Figures

DISCHARGE CELL FOR OPTOGALVANIC SPECTROSCOPY HAVING ORTHOGONAL RELATIONSHIP BETWEEN THE PROBE LASER AND DISCHARGE AXIS

BACKGROUND OF THE INVENTION

1. Origin of the Invention

The invention described herein was made in the performance of work under a NASA Contract and is subject to the provisions of Section 305 of the National Aeronautics and Space Act of 1958, Public Law 85-568 (72 STAT 435; 43 USC 2457).

2. Field of the Invention

This invention relates to a method and apparatus for laser optogalvanic spectroscopy. More particularly, a probe laser beam is directed into a discharge region of a cell wherein low-pressure gas-phase materials to be analyzed are located. The discharge region includes an interelectrode area together with an exterior-electrode area. The gaseous discharge comprises several distinct portions to be analyzed by irradiation with a laser beam. The precise portion to be irradiated by the laser beam is defined by a pair of adjustably moveable electrodes that move closer together, farther apart, or even past the laser beam that is directed through a port in the discharge cell. This invention includes scaling the cell's discharge to be comparable in cross-sectional size to the cross-sectional area of the laser beam. The method of this invention includes optogalvanically studying a selected portion of a gas-phase discharge region by directing a laser beam through a specific area of interest only, and recording signals that are indicative of the absorption of laser radiation by a species within that particular area.

3. Background Discussion

Laser optogalvanic ("LOG") spectroscopy is a sensitive technique used to resolve and record the spectra of gas-phase materials. In LOG spectroscopy, a tunable laser is used to probe the spectral characteristics of atomic or molecular species generated within an electrical discharge in a low pressure gas. Optogalvanic signals arise when the impedance of the discharge changes in response to the absorption of laser radiation. This change in impedance may be conveniently monitored as a change in the voltage across the discharge tube. It is known to form a low-pressure gas discharge between an anode and a cathode and use a laser to irradiate the discharge. The probe laser beam and the longitudinal axis between the electrodes forming the discharge in the prior art were coincidentally aligned.

Such prior art is depicted and explained in detail in connection with FIGS. 1, 2, 7 and 10 in an article entitled *Laser Optogalvanic Spectroscopy of Molecules*, co-authored by me with Dr. Charles T. Rettner, and appearing in a February 1983 issue of "Laser Focus." Since that article also includes a description of my invention as depicted in FIG. 11 it is incorporated by reference herein as though set out in full at this point.

A species being analyzed by prior art devices will absorb laser radiation, as is well known. The amount of absorption is reflected as current or voltage variations in a circuit which includes a voltage source, the electrodes and, of course, the discharge itself.

Prior art LOG systems list a total of only 13 chemical molecules whose spectra have been studied and reported since about 1978, as discussed in the February 1983 "Laser Focus" article. That article discusses the delicate balance involved in obtaining laser optogalvanic signals when a tunable laser is used to probe atomic or molecular species generated within an electrical discharge in a low pressure gas. As there discussed, three conditions must be met: (1) the laser wavelength must match a transition in a species present in the discharge (or flame); (2) the absorption of energy from the laser beam must alter the impedance of the discharge; and (3) a chart recording reflects signals that are indicative of the energy absorption. Such signals and their variation with laser wavelength or frequency are known in the art as LOG spectra. The three stated conditions and apparatus for fulfilling them are well known in the art.

SUMMARY OF THE INVENTION

Disclosed is a method and apparatus for a simple optogalvanic cell which allows signal optimization to be tailored to a wide variety of species. My cell employs a unique orthogonal geometry between a laser probe and a discharge axis, which axis is defined by a pair of spaced apart and longitudinally aligned adjustable electrodes. The moveable electrodes provide a means for adjusting the location of a point to be irradiated by a laser beam crossing the discharge region.

According to my invention the position of the laser beam and the position and cross-section of the discharge region are uniquely adjusted relative to each other by the use of my orthogonal geometry and the dimensions chosen for my apparatus. In a preferred embodiment of my invention, the cell dimensions and the dimensions and configurations of my electrodes are scaled so that the cross-section of the discharge region is comparable in size to the cross-section of the laser beam passing orthogonally through the gas-phase discharge region.

My LOG system is particularly well suited to the detection of unstable species in a gas. Such unstable species are referred to as metastable, radical, or ion species which may be either atoms or molecules. These species can often be generated by the electrical discharge itself. Stable atoms or molecules are also very suitable for study by my invention.

BRIEF SUMMARY OF THE DRAWINGS

FIGS. 2A, 2B and 2C were recorded using a visible dye laser, and FIGS. 2D and 2E an infrared semiconductor diode laser.

DETAILED DESCRIPTION OF THE DRAWINGS

Figure 1:
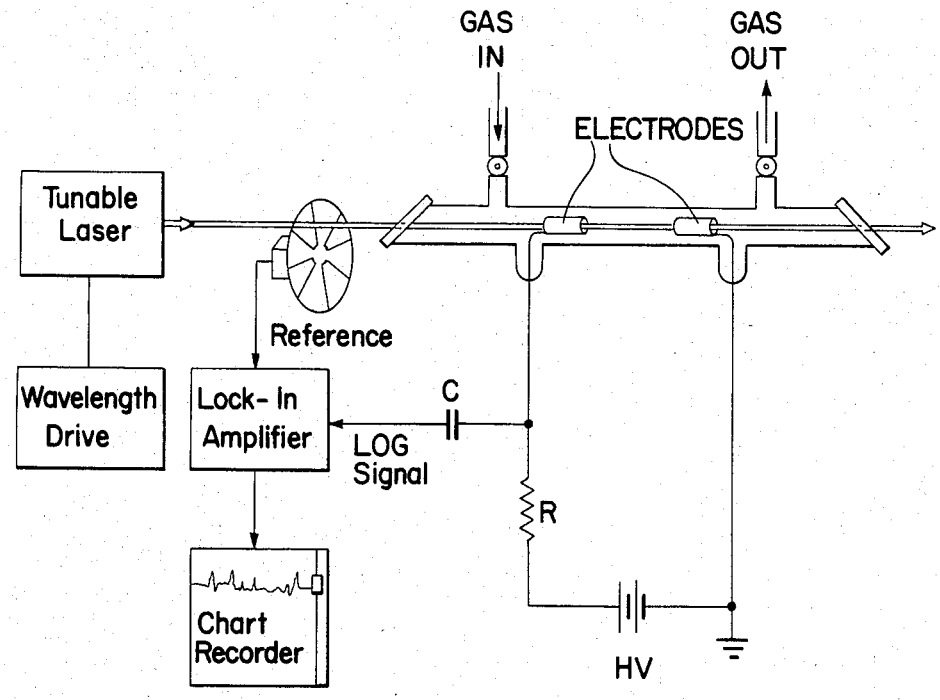
FIG. 1 is a schematic diagram of the prior art depicting a pair of electrodes, a laser beam axis longitudinally aligned with the electrode axis and a typical illustration of a strip chart recorded signal.

FIG. 1 is a prior art diagram that depicts two hollow electrodes, an anode at ground and a cathode at a high negative voltage. As shown in FIG. 1 a CW tunable laser is driven by a wavelength drive. A mechanical chopper, a lock-in amplifier having two inputs and an output driving a chart recorder are employed to monitor current changes induced into the voltage divider circuit connected to the electrodes. The voltage divider supplies voltage to the electrodes and feeds current changes through a coupling capacitor which is connected between the ballast resistor and one input to the lock-in amplifier. All of these components are well known and are available to those of ordinary skill in the art. A description of similar prior art operations involving other lasers and other similar type monitoring circuits is given in the February 1983 Laser Focus article.

In the prior art, the laser beam is coincidentally directed along the axis of the discharge region itself as depicted in FIG. 1. Because the laser beam is absorbed throughout the entire discharge region, the LOG signals are averaged out and do not reflect a distinctive "signature" for any particularly distinct portion within the discharge region.

LOG spectra of a particular gas-phase material in the prior art arrangement of FIG. 1 yield signals that vary in intensity and vary with the wavelength according to the species that is being studied. However, the averaging has severely limited the amount of information that can be derived by prior art laser irradiation.

In my discovery I have relied upon the phenomena that different discharge regions, when irradiated, do produce uniquely individual LOG signals. That is to say, that for a given laser frequency the light energy that is absorbed at different specific locations within the discharge region will yield different LOG signal shapes. The signal shapes will vary in magnitude, polarity and in time relative to a fixed reference. Having discovered this fact, I then relate the LOG signal differences to fundamental discharge physics which are well known. That relation process allows my invention to separate out, from the whole gamut of phenomena, certain primary contributions that are highly probable as the cause for the signal differences.

To give one example, the prior art studies of a pure iodine discharge have long been regarded as a prototype molecule for spectroscopic studies. Much is known about this prototype molecule. I, however, discovered that at different wavelengths of laser light and at different portions of the discharge region, different scientific phenomena were occurring. The occurrence was in turn recordable in the LOG signal shapes and from those shapes a deeper understanding of the iodine discharge and the processes which generate optogalvanic signals has now emerged. Specific examples of my studies of the iodine molecule will be described in more detail after an in-depth description of the distinct portions of a gaseous discharge and the apparatus and method of my invention as depicted by FIGS. 2 through 4.

Figure 2:
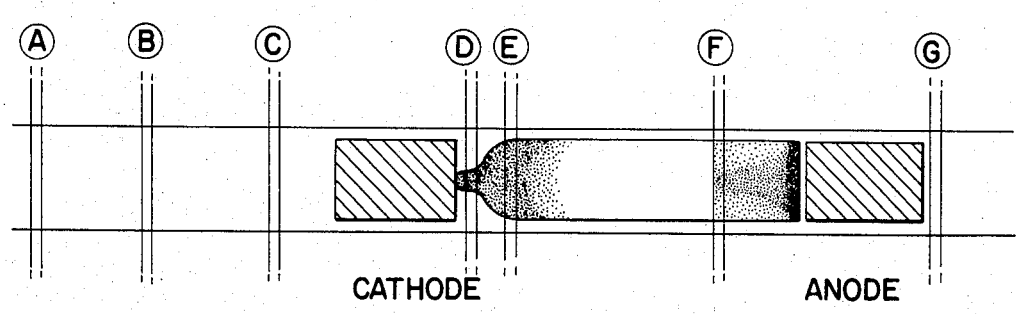
FIG. 2 depicts a gaseous discharge labeled with its distinctive portions.

FIG. 2 depicts a portion of a hollow tube housing an anode and a cathode. A typical gaseous discharge fills the tube and it has the distinctive portions which I have labeled in my FIG. 2. The primary discharge region is located between the electrode pair. In an actual operation the black areas of FIG. 2 glow highly in a relation that black has to white. Thus the cathode dark space is actually darker than the negative glow, which is a bright color; the actual color observed will depend upon the particular gas used in which the discharge is run. These portions of FIG. 2 are typical and serve to illustrate the point that any particular distinctive portion of the entire region may be preselected for irradiation by my orthogonal laser beam. A gas phase is also present outside the interelectrode region, and I have discovered useful information by irradiating that preselected exterior electrode portion as well.

Figure 2A:
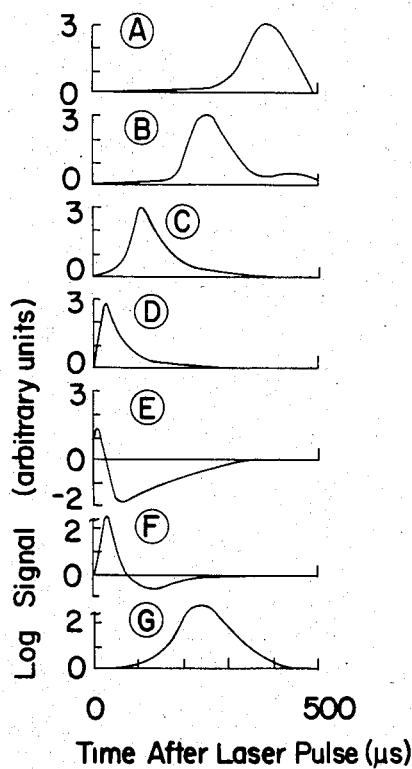
FIGS. 2A, 2B and 2C are signals as recorded on a chart recorder in a study done by using my invention with a pulsed laser irradiating a particular species of gas-phase material.

FIG. 2A is a series of waveforms that are time resolved traces. These traces will be described in more detail hereinafter. Briefly, however, the circled letters of FIG. 2A have corresponding locations in FIG. 2. The points of laser beam irradiation are symbolically shown by the cross-hatching.

Figure 3:
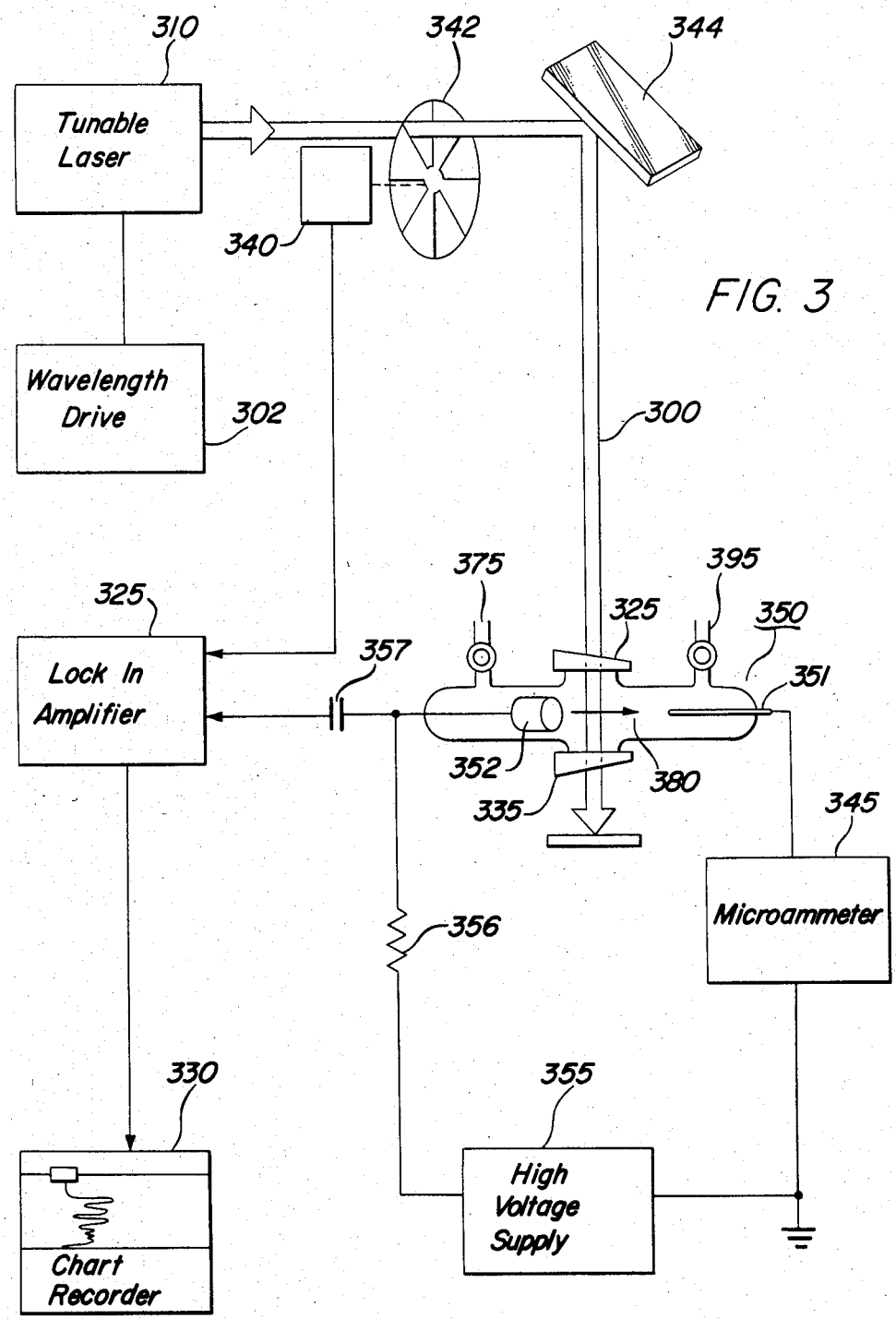
FIG. 3 is a schematic block diagram showing a tunable laser and the orthogonal cell of my invention in highly schematic form.
Figure 4:
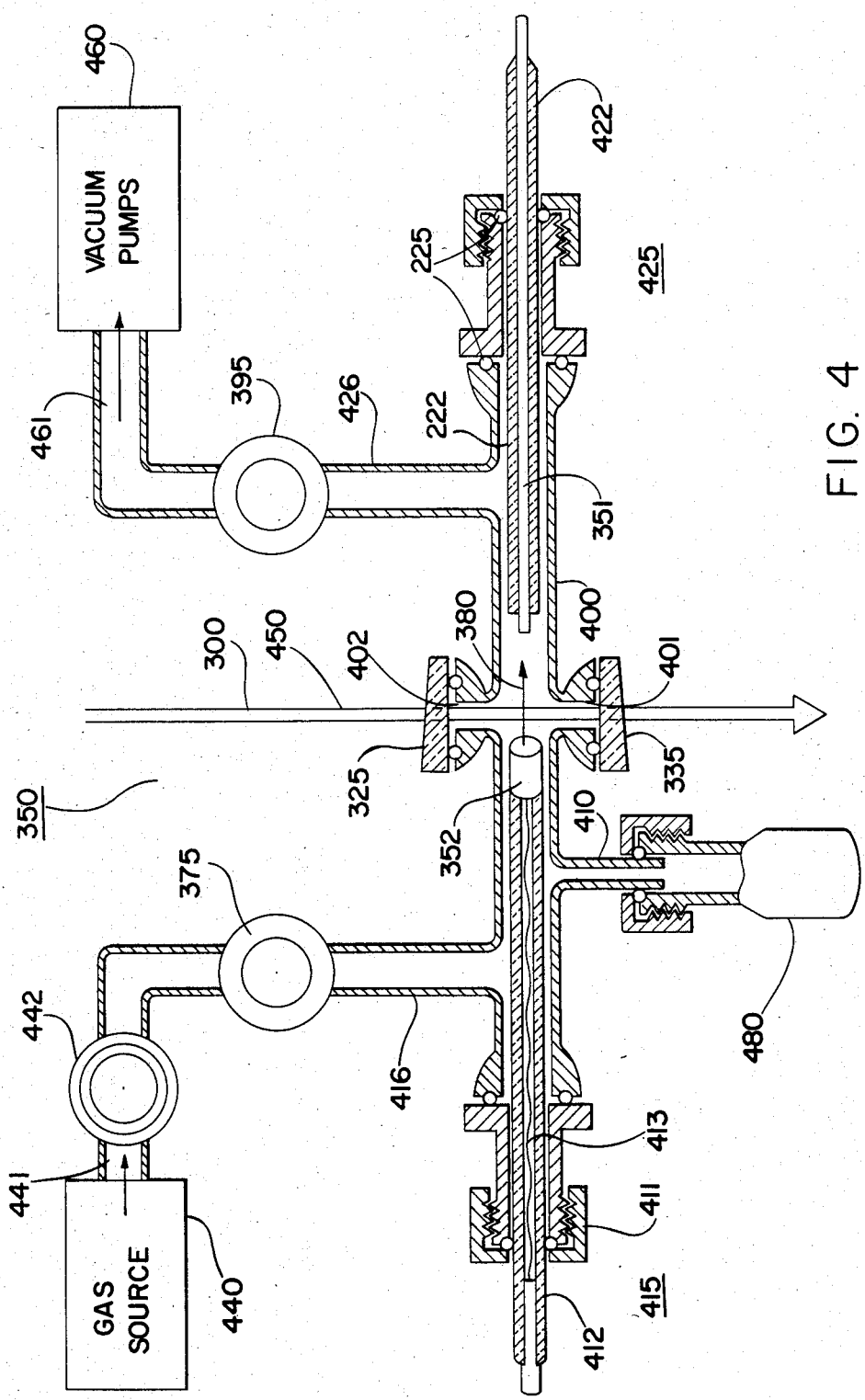
FIG. 4 is a more complete drawing of a direct current discharge optogalvanic cell.

FIG. 3 depicts in schematic form the orthogonal geometry of my invention wherein a laser beam 300 from laser 310 is shown directed vertically into a sealed discharge cell 350. The tunable laser 310 may be of any well known type. It is driven by a variable wavelength frequency drive 302. The tunable laser 310 must be driven over a wide enough frequency range to include the absorption frequency of the particular gas-phase material then under analysis.

Located within cell 350 is an anode 351 which in a preferred embodiment is a tungsten rod. Cathode 352 in cell 350 is, in the preferred embodiment, a hollow molybdenum cylinder. Anode 351 is connected at the grounded side of a suitably chosen high voltage supply 355. Resistor 356 is connected to the positive terminal of source 355 and in turn is connected to cathode 352 and to a coupling capacitor 357. Small current changes will be present on the overriding high direct current supplied by voltage source 355 and the voltage divider action. The voltage divider is comprised of the resistor 356 and the discharge located within cell 350 along axis 380. Quite obviously the discharge at axis 380 is not purely resistive but it may be thought as such for clarity in understanding of the invention.

In a conventional manner chopper 342 and mirror 344 together with the reference signal fed from chopper driver 340 are used to supply a synchronized alternating current operation. The alternating current operation is required for monitoring the small changes in the gaseous discharge at axis 380 in actual operation.

Simply to give an appreciation of the signal magnitudes involved, assume that the discharge is created by a voltage drop across the electrodes of between 300 to 500 volts. A discharge current will normally be less than or equal to 1 milliampere, at a gas pressure in cell 350 of about 0.1 to 5 torr. When a CW dye laser output is tuned to the frequency transition of interest, its output will be in the range of hundreds of milliwatts. In such circumstances the change in the 500 volt discharge will be in the range of tens of millivolts. Thus a sensitive change must be detected. When pulsed lasers are used the changes will be larger, perhaps as much as several volts. These and other parameters are well known in this art.

Returning now to FIG. 3, a pair of inlet and outlet valves 375, 395 are employed to admit a gas-phase material to be studied into cell 350. A gaseous discharge is formed along axis 380 between the anode 351 and cathode 352 at a desired low pressure.

A pair of wedge-shaped laser windows 325, 335 permit proper laser irradiation of the discharge at axis 380.

The windows 325, 335 do not have to be wedgeshaped but are preferred so that optical interference effects, which may degrade the absolute sensitivity, may be avoided. The laser beam 300 will be absorbed by the particular species of gas under study. As it is absorbed the discharge at axis 380 changes in impedance. That change is reflected in a current change which is monitored at the microammeter 345.

Since the amount of impedance change is very slight, I have shown a typical and well known technique for achieving very precise measurements of the changes in cell 350. A reference signal is emitted from chopper source 340 and the current changes indicative of the absorption are fed through capacitor 357 into a synchronous demodulator or sensor 325. The demodulator 325, often termed in the art as a lock-in amplifier, functions to synchronously compare the reference signal (from source 340) with current changes caused by laser energy absorption in cell 350. Those current changes are reflected as the output signal in analog form which, in turn, is supplied to a strip chart recorder 330 operating in a manner well known in the art.

The type of signals to be measured on recorder 330 and the operation for various types of species studied will be explained in greater detail after a more thorough explanation of the structural relationship of my orthogonal cell invention.

FIG. 4 depicts a drawing, not to scale, of a cell whose total length is approximately one foot long. The preferred embodiment of my LOG cell is made primarily from glass. O rings and airtight seals are provided throughout to ensure vacuum operation and to enhance ease of assembly, interchangeability, cleanliness and versatility. The valves and connections are readily available components that are inexpensive and yet provide the assurance that controlled pressures, necessary for LOG studies, are readily available.

The glass cell 350 has several branches. The first main hollow tube 400 has a longitudinal axis to house the cathode assembly 415 and the anode assembly 425. Connected to hollow tube 400 and in airtight communication therewith are an inlet port 416, an outlet port 426, a pressure monitoring port 410 and the orthogonal laser beam guide tube 450. Main tube 400 is made from 0.35 inch inside diameter glass about six inches long.

The laser beam ports 401 and 402, also of glass, have an inside diameter chosen to be about 0.2 inches. Wedge-shaped windows 325 and 335 are sealed by conventional removable clamp means (not shown) and O rings over ports 401 and 402. These laser windows are interchangeable and are selected from materials well known in the art to control the laser irradiation of the proper wavelength that is to be passed through the discharge region. For example, it is well appreciated that window materials are selected along with the selection of different types of lasers to achieve species studies in visible, infrared or ultraviolet light. It is also common practice to avoid having the laser beam hit the sides of the cell wall. I maximize the laser beam interaction with the contained discharge region. Accordingly I have stated that this practical matching of the cross-sections of the beam and of the discharge are substantially the same.

A sample of gas to be studied is admitted from gas source 440 at inlet port 441. The admitted gas passes through a metering needle valve 442. The finely adjustable metering valve 442 is employed together with a variable evacuation rate created by vacuum pump 460 connected to outlet port 461. During this continuous flow operation both of the main glass inlet and outlet valves 375 and 395 are open. The needle valve operation achieves a gentle and controlled flow of gas into cell 350. A controlled low pressure is thus available to permit a gaseous discharge to be formed. Once formed that discharge is stabilized by the needle valve 442 and the setting of a variable exhaust at vacuum pump 460.

An optional operation is to trap a gas within cell 350 by admitting the same through inlet valve 375 and closing both inlet and outlet valves 375 and 395. In either event, a pressure gauge 480 is used at pressure opening 410 to monitor the pressure at its desired amount within cell 350. Pressure gauge 480 may be any well known type such as a calibrated thermocouple gauge or a barometer gauge, as typical examples.

I have discovered that precise information may be achieved by having both the anode 351 and cathode 352 adjustable along axis 380. That adjustment is accomplished at both ends of cell 350 by O ring and threaded connector assemblies. Connector assembly 411 adjustably holds a cathode capillary housing 412 which is made, in a preferred embodiment, from a glass capillary tube of 0.25 inch outside diameter. Inside capillary tube 412 is an electrical connector wire 413. Wire 413 is fastened to a hollow molybdenum cathode cylinder 352 by any suitable mechanical or electrical means. Employment of capillary housing 412 allows the cathode assembly 415 to slide in and out of connector 411. The desired pressure within cell 350 is retained by the O ring seals and the airtight threaded connectors of assembly 411.

In a similar manner anode 351 is housed in a capillary housing tube 422 so that it can sealably slide in and out of the threaded and adjustable connector 421. Obviously it is a matter of choice whether the tungsten rod anode and hollow molybdenum cathode are employed. These should not be taken as exclusive of other more conventional anode/cathode combinations or materials.

OPERATION WITH GAS-PHASE SPECIES

My LOG cell invention is applicable with infrared, visible and ultraviolet spectra for studying atoms, neutral molecules, radicals and ions. Gaseous discharge and flames may be studied at these wavelengths. I have found particularly advantageous the studies of unstable species since these can often be generated by the electrical discharge itself.

Table I lists several species and the relevant data which I have obtained by employing my invention. Table I and my description of the results of my studies confirms the advantageous abilities of adjusting the point of irradiation by my orthogonal geometry. The LOG signals demonstrate that there exists a strong dependence on the results and the precise point of irradiation of the discharge.

Since my invention permits a controlled irradiation at any one of the primary areas depicted in FIG. 1, I have been able to more thoroughly and correctly analyze the results of species studied by using my invention. Stated in a more simple way, I have, with my geometry, been able to isolate the various contributions as reflected in the LOG signals under precisely controlled circumstances. This ability has provided an enhanced understanding together with increased quantitative data.

I will now describe examples of how my invention is employed to achieve results heretofore not isolated nor understood prior to my invention.

TABLE I

| Species Studied | Wavelength (μm) | Application | Region Irradiated |
|---|---|---|---|
| 1. Neutral species: | | | |
| $I_2$ | 0.4–0.7 | maximum signals for wavelength calibration | negative glow (if Stark shifts small) |
| | | multiphoton studies | positive column |
| | | acoustic studies | outside the interelectrode region |
| $NH_3$ | 9.5 | wavelength calibration | positive column or outside the interelectrode region |
| $NO_2$ | 6.2 | | |
| | | electron/molecule/ion interactions | all regions |
| 2. Radical species: | | | |
| $NH_2$ | 0.6 | spectroscopic studies | negative glow only |
| 3. Ion species: | | | |
| $I^-$ | 0.38–0.42 | electron affinity determination | positive column |
| | | ion spectroscopy near photodetechment thresholds | all regions where $[I^-]$ large |

Three types of species are listed in Sections 1, 2 and 3 of Table I. Section 1 is a neutral species. It includes in this representative example iodine, $I_2$, ammonia, $NH_3$, and nitrous oxide, $NO_2$.

Section 2 is an example of a radical species $NH_2$. It is a fragment of $NH_3$ when a hydrogen atom has been lost.

Section 3 is an ion species. In the instance given in this example the iodine molecule $I_2$ has acquired a negative charge and has lost one iodine atom.

All of the species given in Sections 1, 2 and 3 of Table I will have uniquely different spectra. Each spectrum yields a different signal at the chart recorder. The signal differences may be studied and through such studies, physical phenomena may be understood for each of the species.

The power of my invention is readily reflected in Table I. An understanding of that power is appreciated by the material supplied in the vertical columns of the table. The species column has already been described. At the next column on the right the wavelength is given. This wavelength column lists the particular frequency that produced distinctive results in the LOG signal. The third column describes what I term the application of the invention for a particular study. For example, in Section 1 at the visible wavelengths of 0.4 through 0.7 angstroms I detected maximum signal strength at the chart recorder outputs for irradiation of the negative glow region. I could therefore calibrate the tuning frequency of the laser to the known transition frequencies of the iodine molecule. These signals, as shown by the next column, were achieved when the negative glow region only, FIG. 2, was irradiated by the orthogonal laser beam 300.

By sliding the adjustable electrodes 351, 352 to the left in FIG. 4 until the laser beam 300 irradiated the positive column area only of FIG. 2, I obtained different signal characteristics for further interpretive study. Signals resulting from irradiation of this positive column area may be useful for studying multiphoton absorption by the iodine species.

A further observation occurred when I slid both electrodes 351, 352 beyond the laser beam ports 401, 402 until only a region outside the electrodes was irradiated. I list the application in this instance in Table I as an acoustic study. By this I mean that the light energy absorbed from the laser beam has created a pressure change that sweeps through the discharge as an acoustic-like phenomena. For example, the use of a pulsed laser permitted me to measure the time that was required for a peak signal to be detected in the chart recorded output from the reference time when the laser pulse irradiated the discharge. That pressure pulse perturbs the discharge sufficiently that a distinct signal change occurs. I believe a pressure increase occurs with the irradiation and that the pressure increase is caused by degradation of electronic and vibrational energy into translational energy. The process and my findings are more thoroughly explained in a paper listing me as one of the authors and published in Chemical Physics Letters, Vol. 96, No. 3, dated Apr. 8, 1983. That publication, by reference, is incorporated herein as though set forth in full at this point.

For ease of understanding I have reproduced the time-resolved wave shapes from the above-referenced publication in my FIG. 2A. In FIG. 2A each wave shape has been designated by a letter. The letter refers to a particular location for the associated area of the discharge region shown in FIG. 2 which bears those same letters in circles.

As shown by these figures, the further away from the interelectrodes I caused the laser to irradiate, the longer it took to receive a signal. I related the delay time to the time and distance from the negative glow region, FIG. 2. My results compare favorably to the velocity of sound in iodine at room temperature.

The above-described example is described in more detail in the above-referenced paper and need not be elaborated on any further at this point. The example I have given herein shows the advantage of being able to move the interelectrode discharge in a simple, practical manner. This very simple and inexpensive LOG cell invention provides enhanced study capabilities of gaseous materials.

A further publication of which I am a co-author entitled "Infrared Laser Optogalvanic Spectroscopy of Molecules," appearing in Vol. 78, No. 5 of the Journal of Chemical Physics, is incorporated herein by this reference as though set out in full. The referenced article describes in detail some results achieved by use of my invention.

Of importance from that article is the understanding that immediately adjacent to the cathode, FIG. 2, a high voltage drop occurs, a phenomenon well understood in discharge physics. That voltage drop, assuming −500 volts at the cathode, may be as much as several hundred volts just beyond the leading edge of the negative glow region (point Ⓔ), FIG. 2. This high voltage gradient produces associated characteristics which are of interest to the understanding of my invention. Of these characteristics several ones are primary and need further elaboration. The high voltage gradient creates:

(A) High electron density.
(B) High positive ion density.
(C) Low electric field beyond the lower limit area of the gradient's immediate drop.

While much remains to be discovered in this area, I have observed positive and negative polarity signals using my LOG invention in the study of various gas-phase materials. See example signals E and F of FIG. 2. Table II provides a way of making direct comparisons for the signals of FIG. 2A. In operation laser energy of approximately 4 mJ/pulse were employed. The absolute peak intensity of each of the signal traces in FIG. 2A are listed in Table II. I attribute these signal differences to several factors.

TABLE II

PEAK AMPLITUDES OF THE TIME-RESOLVED TRACES IN FIG. 2A

| Trace | Point of Irradiation | Peak Amplitude (mV) |
|---|---|---|
| A | outside discharge | $\leq 1$ |
| B | outside discharge | 2 |
| C | outside discharge | 2 |
| D | negative glow/cathode dark space | 150 |
| E | negative glow | 15, −20 |
| F | Faraday dark space/positive column | 40, −20 |
| G | outside discharge | 3 |

Irradiation at points outside the discharge (Ⓐ, Ⓑ, Ⓒ, Ⓖ) produced relatively weak signals which were delayed from the laser pulse by an amount apparently proportional to the distance to the negative glow. As the delay increased, the LOG pulse broadened. Within the discharge region, strong signals were observed but with a complex shape which showed changes in polarity through the time profile.

To study the effects of increased laser energy, four locations were chosen for further study: two outside the discharge, Ⓑ and Ⓒ, and two within the discharge, Ⓔ and Ⓕ (see FIG. 2). At point Ⓑ, the peak amplitude of the relatively weak signal increased by a factor of ten as the laser energy was increased from 2 to 20 mJ, with no change in the shape of the signal.

Figure 2B:
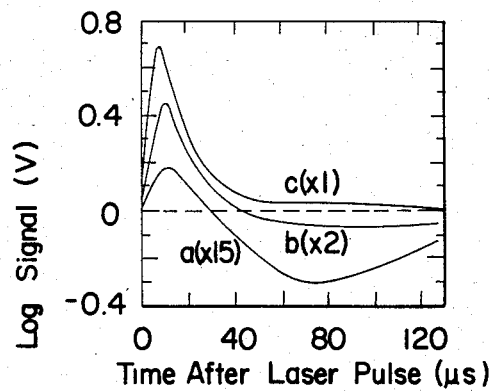

The signal at point Ⓒ showed a more complex dependence on pulse energy as shown in FIG. 2B. Within the first 10 μs a positive pulse was observed which appeared to increase exponentially while at later times, $\approx 100$ μs, the positive signal had a linear dependence on the laser energy.

Figure 2C:
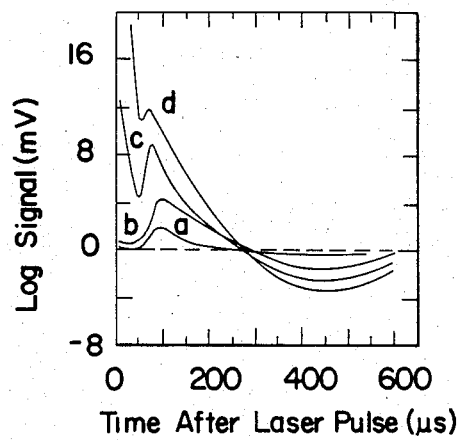

The temporal profiles following irradiation in the negative glow at point Ⓔ shown in FIG. 2C. At 4 mJ the integrated signal was negative since the main component was a broad negative pulse with a peak near 75 μs. However, at 16 mJ the positive contribution at short times dominated, thus producing a signal whose integral was positive. At the remaining location, Ⓕ, the basic time profile was insensitive to changes in laser energy between 4 and 16 mJ except for a fast, $\leq 10$ μs, positive component which appeared at the highest energies.

Figure 2D:
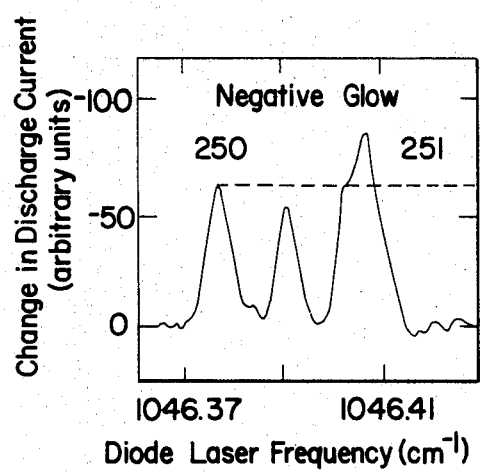
FIGS. 2D and 2E are similar signals using a continuous wave laser rather than a pulsed laser. These figures also demonstrate the wide range of wavelengths which can be used.
Figure 2E:
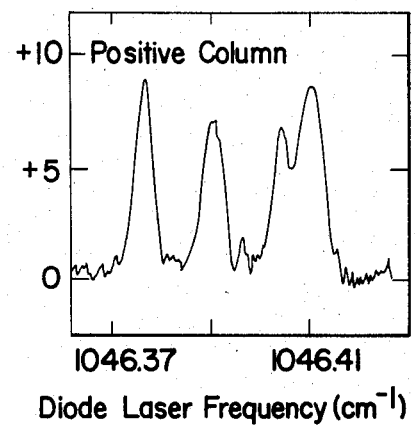

FIGS. 2A, 2B and 2C have been described using a pulsed laser. FIGS. 2D and 2E will now be described using a continuous wave laser which is tuned variably through the limited wavelengths example shown in FIGS. 2D and 2E. The stated conditions for these two latter figures are identical to comparable positions of the pulsed laser example; except, of course, the variable and continuous laser is being employed.

Turning now more particularly to FIG. 2D, as the wavelength of the continuous laser is increased in frequency to approximately 1046.37 cm$^{-1}$, the change in discharge current at about the negative glow region at location E, FIG. 2, begins to increase in the negative amount which reaches a peak at approximately −60 on a relative scale. Thereafter as the laser frequency is continuously increased in frequency the other negative peaks as shown in FIG. 2D are achieved. These peaks observed correspond to known absorption frequencies of the NH$_3$ molecule. It should be understood that, if, for example at point 250, FIG. 2D, the wavelength of a continuous wave laser was stopped and not varied further for a time T, then the LOG signal would hold the peak level as shown, for example, by the dashed line 251 of FIG. 2D. In either event, this FIG. 2D is thus a real time picture of a typical LOG signal under the stated conditions.

FIG. 2E shows the same continuous wave laser scanned over the same frequency limits. However, for FIG. 2E and using the optogalvanic geometry of my invention, the laser beam has been moved to the positive column Location F, FIG. 2. In this instance at essentially the same frequency noted in FIG. 2D the change in the discharge current is positive by a smaller amount than was true in the negative glow region for FIG. 2D. When the change in the discharge current is reflected in the LOG signal as positive value signal I reference it as an increase in the discharge current. It is clear from the same scale drawing of both FIG. 2D and FIG. 2E, that at the positive column location there is a decided increase of the discharge current at the specified wavelengths for the continuous wave laser as compared with the value noted at the point for the negative glow region.

Digressing for a moment, at any one of these peaks, the frequency of a pulsed laser would be set. For example, with reference to FIG. 2D a pulsed laser would be set with a fixed frequency at the wavelength indicated by peak 250.

I will now describe some observations which have resulted from employing the optogalvanic principles of my invention as claimed, to study the neutral species NH$_3$ and NO$_2$ in the infrared region.

Positive signals observed in the infrared LOG studies (such as NH$_3$ and NO$_2$ from Section 2 of Table I) result from an increase in kinetic energy of species located in the negative glow of the discharge. For irradiation outside the interelectrode region or away from the negative glow the energy absorbed as rovibrational quanta is degraded to translational energy through V-T transfer in a time fast compared to the bulk energy transfer time to the discharge region. The positive signals produced therefore result from an increase in the translational energy (temperature) of species in the negative glow. However, when directly irradiating this region, vibrationally excited species will be produced in the discharge, the mean concentration depending on the relaxation times involved. It is believed that the negative signals observed result from an increase in (principally) the vibrational energy of species in the negative glow.

It should be noted that, for positive signals, the size of the NH$_3$ signal at 9.5 m was typically three to five times smaller than that measured for NO$_2$ at 6.2 m, per mW of absorbed laser power. These signals are similar in magnitude to those observed in I$_2$ at 0.59 m for equivalent incident laser power, which suggests that the important effect is the deposition of energy into the discharge.

An estimate of the ratio of the increase in the mean kinetic energy of the gas due to the laser energy absorbed in a half-cycle of the chopping period (assuming adiabatic conditions during this period) to the mean kinetic energy of the gas produces a number in good agreement with the ratio of the resulting change in discharge impedance to the discharge impedance, i.e., about 1 part in 10$^6$.

Of the numerous possible electron/atom/molecule interactions I consider the following factors to be most probable: ionization by electron impact, electron attachment, and direct and dissociative electron-ion and ion-ion recombination. Electrons are lost in a glow discharge through negative ion formation (attachment), electron diffusion, mutual repulsion and recombination. Electron attachment and recombinatin are particularly important in the negative glow, perturbation of this region, I propose, being crucial to the generation of the LOG signal.

In the region comprising the negative glow, the cathode dark space, and the cathode glow, the voltage gradient, the net charge density, and the electron and ion density all have their maximum values. The slow electrons entering the negative glow produce this luminous region by undergoing numerous excitation collisions which leave the electrons with very low kinetic energies. In the negative glow the combination of the high electron and ion densities and the low electric field allows recombination and electron attachment reactions to be important processes in this region of the discharge, even though in the low current (<1 mA) discharges employed in using my invention, ambipolar diffusion may dominate the overall loss processes for charged species. It is likely that the positive signals observed result from the reduced efficiency with increasing gas kinetic temperature, of the ion-ion recombination.

$$A^+ + B^- \rightarrow A + B$$

or the direct electron-ion recombination $$A^+ + e^- \rightarrow A + h\nu.$$

The conventional models of ion-ion recombination, whether occurring in the presence or absence of a (neutral) third body, predict a recombination coefficient which decreases with increasing ion temperature, as is reported in, for example, A. Von Engel's "Ionized Gases," published by Claredon, Oxford, 1965. When the increased neutral kinetic temperature propagates into the discharge region, the ion temperature is increased through collisional energy transfer. The effectiveness of these processes increases the larger the attractive electrostatic energy becomes relative to the kinetic energy. A reduction in the depletion rate of the positive ion population in the negative glow increases the probability of energetic ion bombardment of the cathode, thus a positive current signal is expected.

Another possible cause of the positive signals which were observed is the electron impact ionization process $$A + e^- \rightarrow A^+ + 2e^-$$

and its increased efficiency with increasing electron temperature. This mechanism suggests that, in a similar manner to that proposed for atomic systems (R. A. Keller and E. F. Zalewski, Appl. Opt. 19, 3301 (1980)), the energy supplied to the molecular system by irradiation is ultimately transferred to the electron gas through the numerous electron collisions. However, for irradiation outside the discharge region, the initial transfer of energy must proceed via intermolecular collisions. For low-energy discharges like that used in studies performed by use of my invention, the cross-sections for ionization by electron impact increase with increasing electron temperature and would produce a decrease in the discharge impedance, as observed for positive signals.

The negative signals which correspond to an increase in the discharge impedance are believed to result from a large enhancement in the electron attachment rate when the negative glow region is irradiated by the resonant infrared power. Electron attachment to molecules $$A + e^- \rightarrow A^-,$$

which is an important process occurring in discharges of electronegative gases like $NO_2$, $I_2$, and $NH_3$ is known to be particularly sensitive to thermal effects (R. N. Compton, *Proceedings of the Eleventh International Conference on the Physics of Electronic and Atomic Collisions* (North-Holland, Amsterdam, 1980)). The attachment cross-sections may increase or decrease with increasing electron energy depending on the mean electron energy, which may be <1 eV at the negative glow or a few eV in the positive column of low-current glow discharges. For molecules, the dependence on internal vibrational energy content may be large: heating $N_2O$, e.g., excites higher vibrations which have good Franck-Condon overlap with the $N_2O$ ground electronic state, producing an increase in the attachment cross-section. The dissociative attachment in molecular iodine (H. L. Brooks, S. R. Hunter, and K. J. Nygaard, J. Chem. Phys. 71, 1870 (1979)) also increases with increasing temperature, due to the increasing population of upper vibrational states.

It should be emphasized that the kinetic energy dependence of many processes occurring within an electrical discharge often depends on the specific molecular (ion) potential energy surfaces involved, and that this dependence may vary dramatically if curve crossings (leading, e.g., to predissociation) occur.

Recombination collisions occur several orders of magnitude more often than indicated by kinetic theory due to the strong electrostatic attractions involved. Study of the dependence of both the positive and negative signals observed on the chopping frequency may provide enough time-resolution to extract the role played by vibrational relaxation in the recombination and attachment processes. This would allow the proposed dependence of the optogalvanic signals on these processes to be further tested.

What I have concluded is that the prior art's use of laser irradiation coincidentally along the discharge axis masks the many distinct signals that are achieved by using my invention's orthogonal geometry. Use of my invention has, for the first time, provided an optogalvanic study of distinct discharge portions, and allowed the direct and quantitative comparison between signals associated with each discharge region. The method and apparatus of this invention thus provides new and improved understanding of species within a discharge region.

The above description presents the best mode contemplated in carrying out the present invention. This invention is, however, susceptible to modifications and alternate constructions from the embodiments shown in the drawings and described above. Consequently, it is not the intention to limit the invention to the particular embodiments disclosed. On the contrary, the invention is to cover all modifications, sizes and alternate constructions falling within the spirit and scope of the invention as expressed in the appended claims.

What is claimed is:

1. A laser optogalvanic (LOG) spectrometer, comprising:
   a cell containing a gas-phase material at a low pressure;
   means for creating a gaseous discharge region along one axis of said cell which discharge region comprises distinctly different discharge portions;
   means for producing a single laser energy beam collimated orthogonally to intersect said discharge axis at preselected ones of said distinctly different discharge portions;
   means for recording signals indicative of the interaction between said laser beam and said preselected portions of said discharge region;
   said cell comprising a hollow longitudinal glass tube having a pair of electrodes housed therein and means for applying a discharge creating voltage to said pair of electrodes to form said discharge having said distinctly different portions along the longitudinal axis of said hollow tube;
   means for sealably holding the pair of electrodes in said glass tube and adjustably sliding either or both of said electrode pair along said longitudinal axis, and
   means for containing said gaseous discharge along said longitudinal axis with the discharge having a cross-sectional area substantially comparable in size to that of said laser beam.

2. A LOG spectrometer in accordance with claim 1 and wherein said cell further comprises:
   a second hollow glass tube orthogonally joined with said first tube; and
   a pair of removably sealed laser windows at the ends of said second glass tube.

3. A LOG spectrometer in accordance with claim 2 and further comprising:
   O ring seals held in compression between the ends of the second hollow tube and said laser windows.

4. A LOG spectrometer in accordance with claim 1 and further comprising:
   a gaseous discharge having a negative glow region as one of said distinct portions; and
   means for positioning said negative glow region only to be irradiated by said laser beam.

5. A laser optogalvanic (LOG) spectrometer, comprising:
   a cell including a hollow longitudinal glass tube containing a gas-phase material at a low pressure;
   means for creating a gaseous discharge region along one axis of said cell, which discharge region comprises distinctly different discharge portions;
   means for producing a laser energy beam collimated orthogonally to intersect said discharge axis at preselected ones of said distinctly different discharge portions;
   said gaseous discharge region including a negative glow region as one of said distinct portions;
   said laser beam having a given cross-sectional area;
   means for containing said gaseous discharge along a longitudinal axis having a cross-sectional area substantially comparable in size to that of said laser beam, and
   said containing means including;
   a first capillary tube smaller in diameter than said glass tube;
   a hollow cylindrical cathode having an electrical conductor connected thereto with the cathode mounted on the capillary and a connector extending from the capillary for connection to a voltage source;
   first means slideably sealing the first capillary tube in one end of said hollow glass tube;
   a second capillary tube smaller in diameter than said glass tube and containing an anode rod extending therethrough and out both ends, and
   second means slideably sealing the second capillary tube in the opposite end of said hollow glass tube.

6. A method of obtaining a laser optogalvanic (LOG) spectrum comprising the steps of:
   containing a gas phase material within a container to be studied at a preselected pressure;
   creating a gaseous discharge region from said gas-phase material along a discharge axis, which discharge region comprises distinctly different discharge portions;
   directing a laser energy beam orthogonally through said discharge axis for interaction with said gaseous discharge region;
   controlling the cross-sectional area of said laser beam, and containing said gaseous discharge along a longitudinal axis having a cross-sectional area substantially comparable in size to that of said laser beam.

7. A LOG spectrum method in accordance with claim 6 wherein said discharge-creating step further comprises:
   sealably holding a pair of electrodes along one axis in said container; and
   adjustably sliding either or both of said electrode pair along said one axis.

8. A LOG spectrum method in accordance with claim 6 wherein said gaseous discharge having a negative glow region as one of said distinct portions, and further comprising the step of:
   positioning said negative glow region only for irradiation by said laser beam.

* * * * *